United States Patent [19]

Drabek et al.

[11] 4,386,101
[45] May 31, 1983

[54] UNSYMMETRICAL BIS-CARBAMATES AND THEIR USE FOR COMBATING PESTS

[75] Inventors: Jozef Drabek, Oberwil, Switzerland; Manfred Böger, Weil am Rhein, Fed. Rep. of Germany

[73] Assignee: Ciba-Geigy Corporation, Ardsley, N.Y.

[21] Appl. No.: 319,865

[22] Filed: Nov. 9, 1981

[30] Foreign Application Priority Data

Nov. 20, 1980 [CH] Switzerland ................. 8590/80
Dec. 30, 1980 [CH] Switzerland ................. 9643/80
Sep. 25, 1981 [CH] Switzerland ................. 6206/81

[51] Int. Cl.³ .............. A01N 47/22; C07D 307/86
[52] U.S. Cl. ............................ 424/285; 424/251; 424/258; 424/269; 424/273 P; 424/278; 424/282; 544/315; 544/317; 546/156; 548/264; 548/377; 549/435; 549/438; 549/448; 549/454; 549/470; 560/134; 560/135; 560/136; 560/137
[58] Field of Search .......... 260/340.5 R, 340.9 R, 260/346.73; 544/315, 317; 546/156; 548/264, 548/377; 560/134, 135, 136, 137; 424/251, 258, 273, P, 269, 278, 282, 285

[56] References Cited

U.S. PATENT DOCUMENTS 3,857,860 12/1974 Kulhe et al. ................. 260/346.73

FOREIGN PATENT DOCUMENTS 2132936 1/1973 Fed. Rep. of Germany.

Primary Examiner—Henry R. Jiles
Assistant Examiner—Bernard Dentz
Attorney, Agent, or Firm—Frederick H. Rabin

[57] ABSTRACT

Unsymmetrical bis-carbamates of the formula

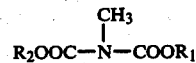

wherein $R_1$ is a phenyl, dihydrobenzofuranyl, naphthyl, pyrimidyl, pyrazolyl, triazolyl, quinolinyl or tetrahydroquinolinyl group, and $R_2$ is a benzyl group, processes for producing them and their use for combating pests are described.

10 Claims, No Drawings

UNSYMMETRICAL BIS-CARBAMATES AND THEIR USE FOR COMBATING PESTS

The present invention relates to unsymmetrical bis-carbamates, to processes for producing them, and to their use for combating pests.

The unsymmetrical bis-carbamates have the formula

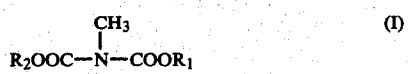

wherein $R_1$ is a phenyl, dihydrobenzofuranyl, naphthyl, pyrimidyl, pyrazolyl, triazolyl, quinolinyl or tetrahydroquinolinyl group, and $R_2$ is a benzyl group.

The groups denoted by $R_1$ and $R_2$ can be unsubstituted or mono- or polysubstituted. Examples of substituents on the $R_1$ and $R_2$ groups are in particular: $C_1$–$C_4$-alkyl, $C_1$–$C_4$-alkoxy, $C_1$–$C_4$-alkylthio, $C_1$–$C_4$-alkoxy-$C_1$–$C_4$-alkyl, such as ethoxymethyl, $C_1$–$C_4$-alkylthio-$C_1$–$C_4$-alkyl, such as ethylthiomethyl,

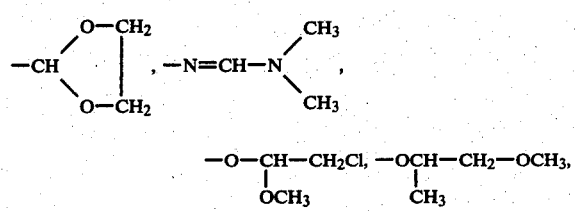

halogen, amino, methylamino, dimethylamino, cyano or nitro. The phenyl group can also be substituted in the 2,3- or 3,4-position, especially in the 2,3-position, by the group

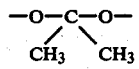

or —O—CH$_2$—O—. By halogen is meant here fluorine, chlorine, bromine or iodine, particularly however chlorine.

Compounds of the formula I preferred on account of their action are those wherein $R_1$ is 2,2-dimethyl-2,3-dihydrobenzofuranyl or naphthyl, or phenyl which is unsubstituted or mono- or polysubstituted by $C_1$–$C_4$-alkyl, $C_1$–$C_4$-alkoxy, $C_1$–$C_4$-alkoxy-$C_1$–$C_4$-alkyl, $C_1$–$C_4$-alkylthio-$C_1$–$C_4$-alkyl or dimethylamino, or by

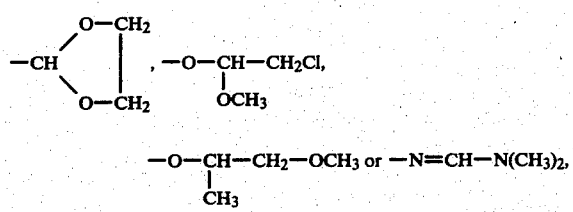

or phenyl substituted in the 2,3-position by

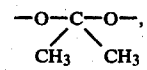

and $R_2$ is benzyl which is unsubstituted or mono- or polysubstituted by halogen, $C_1$–$C_4$-alkyl, $C_1$–$C_4$-alkoxy or nitro, or benzyl substituted in the 2,3-position by —O—CH$_2$—O—.

Particularly preferred compounds of the formula I are those wherein $R_1$ is 2,2-dimethyl-2,3-dihydrobenzofuranyl or naphthyl, or phenyl which is unsubstituted or mono-, di- or trisubstituted by $C_1$–$C_4$-alkyl, $C_1$–$C_4$-alkoxy, ethylthiomethyl, ethoxymethyl, dimethylamino,

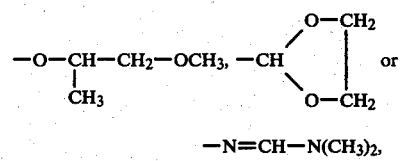

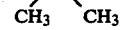

or phenyl substituted in the 2,3-position by 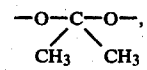, and $R_2$ is benzyl which is unsubstituted, or mono- or polysubstituted by halogen, nitro, methyl or methoxy, or benzyl substituted in the 2,3-position by —O—CH$_2$—O—.

More particularly preferred however are compounds of the formula I wherein $R_1$ is 2,2-dimethyl-2,3-dihydrobenzofuranyl, and $R_2$ is benzyl which is unsubstituted or monosubstituted by chlorine, methyl, methoxy or nitro, or benzyl substituted in the 2,3-position by —O—CH$_2$—O—.

The compounds of the formula I can be produced by methods known per se, for example as follows:

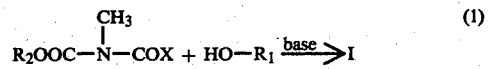

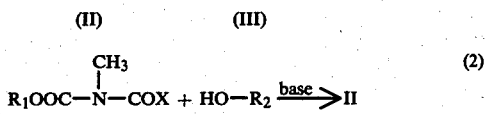

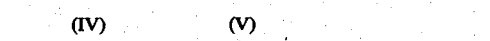

In the formulae II, III, IV and V, the symbols $R_1$ and $R_2$ have the meanings defined under the formula I; and X in the formulae II and IV is a halogen atom, particularly a chlorine atom.

The processes are performed at a reaction temperature of between $-50°$ C. and $+130°$ C., preferably between $-10°$ C. and $+100°$ C., under normal or slightly elevated pressure, and in the presence of a solvent or diluent inert to the reactants.

Suitable bases for the processes are in particular: tertiary amines, such as trialkylamine, pyridines and dialkylanilines, also hydroxides, oxides, carbonates and bicarbonates of alkali metals and alkaline-earth metals, as well as alkali metal alcoholates, for example potassium-tert-butylate and sodium methylate.

Solvents or diluents which are suitable are for example: ethers and ethereal compounds, such as diethyl ether, diisopropyl ether, dioxane or tetrahydrofuran; aliphatic and aromatic hydrocarbons, especially benzene, toluene or xylenes; and ketones, such as acetone, methyl ethyl ketone and cyclohexanone.

The starting materials of the formulae II to V are known, or they can be produced by methods analogous to known methods.

The compounds of the formula I are suitable for combating pests on animals and plants. They are suitable in particular for combating insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera; and for combating mites and ticks of the order Acarina. The compounds of the formula I are above all suitable for combating insects that damage plants, especially insects that damage plants by eating, in crops of ornamental plants and productive plants, particularly in cotton crops (for example against Spodoptera littoralis and Heliothis virescens), and in vegetable crops (for example against Leptinotarsa decemlineata and Myzus persicae). It is to be emphasised in this connection that the stated compounds are characterised both by a strongly marked systemic as well as contact action against sucking insects, especially against sucking insects of the order Homoptera, and in particular against insects of the Aphididae family (for example Aphis fabae, Aphis craccivora and Myzus persicae), which are very difficult to combat by means hitherto known. Active substances of the formula I exhibit also a favourable action against flies, such as Musca domestica, and against mosquito larvae. The compounds of the formula I are also distinguished by a broad ovicidal and ovilarvicidal activity. Furthermore, the compounds of the formula I have fungicidal and plant-growth-regulating properties, and have a valuable action against phytoparasitic nematodes, as well as against ectoparasitic mites and ticks, for example those of the families: Ixodidae, Argasidae and Dermanyssidae.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutylor dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publication: "Mc Cutcheon's Detergents and Emulsifers Annual", MC Publishing Corp., Ringwood, N.J., 1979.

The pesticidal preparations contain as a rule 0.1 to 99%, particularly 0.1 to 95%, of active substance of the formula I, 1 to 99.9% of a solid or liquid additive, and 0 to 25%, especially 0.1 to 25%, of a tenside. Whereas commercial products are preferably in the form of concentrated compositions, the compositions employed by the end-user are as a rule diluted.

The compositions can also contain additives such as stabilisers, antifoam agents, viscosity regulators, binders and adhesives, as well as fertilisers or other active substances for obtaining special effects.

Formulation examples for liquid active substances of the formula I (%=percent by weight)

| 1. Emulsion concentrates | (a) | (b) | (c) |
|---|---|---|---|
| active substance, | 20% | 40% | 50% |
| calcium dodecylbenzenesulfonate | 5% | 8% | 5.8% |
| castor oil-polyethylene glycol ether (36 mols of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any required concentration can be produced from concentrates of this type by dilution with water.

| 2. Solutions | (a) | (b) | (c) | (d) |
|---|---|---|---|---|
| active substance | 80% | 10% | 5% | 95% |
| ethylene glycol-monomethyl ether | 20% | — | — | — |
| polyethylene glycol M G 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of the smallest possible drops.

| 3. Granulates | (a) | (b) |
|---|---|---|
| active substance | 5% | 10% |
| kaolin | 94% | — |
| highly dispersed silicic acid | 1% | — |
| attapulgite | — | 90% |

The active substance is dissolved in methylene chloride, the solution is sprayed onto the carrier, and the solvent is subsequently evaporated off in vacuo.

| 4. Dusts | (a) | (b) |
|---|---|---|
| active substance | 2% | 5% |
| highly dispersed silicic acid | 1% | 5% |
| talcum | 97% | — |
| kaolin | — | 90% |

Ready-for-use dusts are obtained by the intimate mixing together of the carriers with the active substance.

Formulation examples for solid active substances of the formula I (%=percent by weight)

| 5. Wettable powders | (a) | (b) |
|---|---|---|
| active substance | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active substance is well mixed with the additives and the mixture is thoroughly ground is a suitable mill. Wettable powders which can be diluted with water to give suspensions of the required concentration are obtained.

| 6. Emulsion concentrates | |
|---|---|
| active substance | 10% |
| octylphenol polyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| active substance | 5% | 8% |
| talcum | 95% | — |
| kaolin | — | 92% |

Dusts ready for use are obtained by mixing the active substance with the carrier and grinding the mixture in a suitable mill.

| 8. Extruder granulate | |
|---|---|
| active substance | 10% |
| sodium lignin sulfonate | 2% |
| carboxymethylcellulose | 1% |
| kaolin | 87% |

The active substance is mixed and ground with the additives, and the mixture is moistened with water. This mixture is extruded and then dried in a stream of air.

| 9. Coated granulate | |
|---|---|
| active substance | 3% |
| polyethylene glycol (M G 200) | 3% |
| kaolin | 94% |

The finely ground active substance is evenly applied, in a mixer, to the kaolin moistened with polyethylene glycol. Dustfree coated granulates are obtained in this manner.

| 10. Suspension concentrates | |
|---|---|
| active substance | 40% |
| ethylene glycol | 10% |
| nonylphenolpolyethylene glycol ether | |
| (15 mols of ethylene oxide) | 6% |
| sodium lignin sulfonate | 10% |
| carboxymethylcellulose | 1% |
| 37% aqueous formaldehyde solution | 0.2% |
| silicon oil in the form of a | |
| 75% aqueous emulsion | 0.8% |
| water | 32% |

The finely ground active substance is intimately mixed with the additives. There is thus obtained a suspension concentrate from which can be produced, by dilution with water, suspensions of the concentration required.

EXAMPLE 1

Production of benzyl-(2,2-dimethyl-2,3-dihydrobenzofuranyl)-N-methyl-bis-carbamate To a solution of 9.93 g of chlorocarbonyl-N-methyl-(2,2-dimethyl-2,3-dihydrobenzofuranyl)-carbamate in 100 ml of toluene are added dropwise at 0° C. 3, 78 g of benzyl alcohol and subsequently 4.85 ml of triethylamine. The reaction mixture is stirred for 8 hours at 20° C. and for 2 hours at 50° C.; and is then washed three times with 100 ml of water each time. The organic layer is separated, and dried with sodium sulfate. The toluene is distilled off to thus obtain the compound of the formula

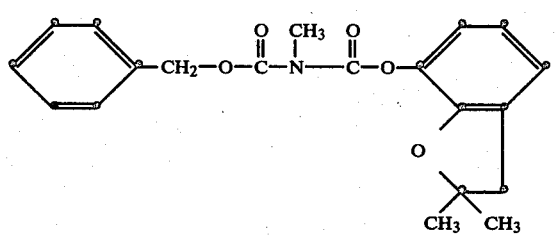

having a refractive index of $n_D° = 1.5497$.

The following substances are produced in the same manner:

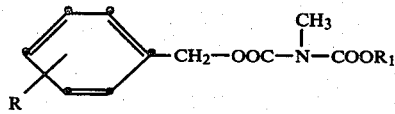

| R | $R_1$ | Physical data |
|---|---|---|
| 4-NO$_2$ | 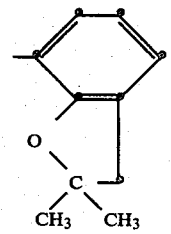 | m.p.: 119–121° C. |
| H | 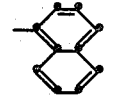 | $n_D^{20°}$: 1,6007 |
| H | 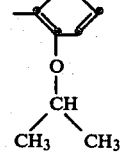 | $n_D^{20°}$: 1,5381 |
| H | 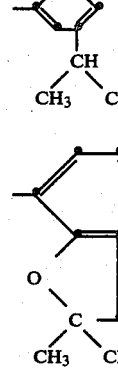 | $n_D^{20°}$: 1,5417 |
| 4-CH$_3$O— | | $n_D^{20°}$: 1,5506 |
| 4-Cl— | 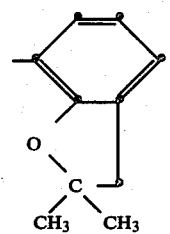 | $n_D^{20°}$: 1,5532 |
| 2-CH$_3$— | 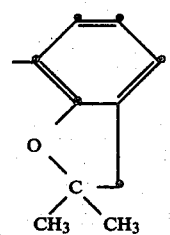 | $n_D^{20°}$: 1,5479 |

-continued $$R-\text{benzene ring}-CH_2-OOC-N(CH_3)-COOR_1$$

| R | R₁ | Physical data |
|---|---|---|
| H | (1,3-dioxolane: CH attached via O-CH₂-CH₂-O ring) | $n_D^{20°}$: 1,5521 |
| H | pyrazole: -CH=C(CH₃)-N(C₃H₇(i))-N= (1-isopropyl-3-methylpyrazol-4-yl) | $n_D^{20°}$: 1,5258 |
| H | pyrimidine: CH₃-C=CH-C(CH₃)=N-C(N(CH₃)₂)=N- | m.p.: 91–95° C. |
| H | thiadiazole: -C(=N-N(C₂H₅))-C(S-C₂H₅)=N- | $n_D^{20°}$: 1,5432 |
| 2,3-O—CH₂—O— | benzene ring with -O-C(CH₃)₂- (isopropylidenedioxy) | $n_D^{20°}$: 1,5578 |

EXAMPLE 2

Insecticidal stomach-poison action: *Laspeyresia pomonella*

Feed cubes were sprayed with a test solution containing the given concentration of the compound to be tested. After the drying of the coating, larvae of the species Laspeyresia pomonella (L₁ stage) were settled onto the feed cubes. Two cubes were used per test compound, and an evaluation of the attained mortality rate was made after 48 hours. The test was carried out at 24° C. with 60% relative humidity.

The compounds according to the Production Example 1 exhibited against the species Laspeyresia pomonella the level of activity shown in the Table which follows.

EXAMPLE 3

Insecticidal contact action: *Myzus persicae*

Plants (*Vicia fabae*) grown in water were each infested before commencement of the test with about 200 individuals of the Myzus persicae species. The plants treated in this manner were sprayed dripping wet 3 days later with a solution containing 10 and 1 ppm, respectively, of the compound to be tested, from a distance of 30 cm. Two plants were used per test compound and per concentration, and an assessment of the mortality rate attained was made after a further 24 hours.

Compounds according to Example 1 exhibited against the species Myzus persicae the activity shown in the following Table.

EXAMPLE 4

Insecticidal systemic action: *Aphis craccivora*

Rooted bean plants were transplanted to pots each containing 600 ccm of soil; and 50 ml of a test solution containing 25 ppm, 5 ppm and 1 ppm, respectively, of the compound to be tested was subsequently poured directly onto the soil. After 24 hours, aphids (Aphis craccivora) were settled onto the parts of plants above the soil, and a plastics cylinder was placed over each plant and drawn to by tying at the bottom in order to protect the aphids from any contact or gas action of the test substance. An evaluation of the mortality rate achieved was made 24 and 48 hours after commencement of the test. Two plants, each in a separate pot, were used per concentration level of test substance. The test was carried out at 25° C. with 70% relative humidity.

Compounds according to Example 1 exhibited against insects of the species Aphis craccivora the activity shown in the following Table.

Biological test results

In the following Table are summarised test results based on the Examples given in the foregoing, the index of values with regard to the percentage mortality of the pests being as follows:

| Compound $\text{R}\text{—}\underset{\text{R}}{\bigcirc}\text{—CH}_2\text{—OOC}\text{—}\underset{\underset{\text{CH}_3}{|}}{\text{N}}\text{—COOR}_1$ | | Activity against | | |
|---|---|---|---|---|
| | | *Laspeyresia pomonella* | *Myzus* | *Aphis* |
| R | $R_1$ | $L_1$-larvae | *persicae* | *craccivora* |
| 4-NO$_2$ | phenyl with 2-CH$_3$ and 3-O–C(CH$_3$)$_2$– (2,2-dimethylbenzodioxole-type) | E | A | B |
| H | benzodioxole | F | C | B |
| H | 2-CH$_3$-phenyl-O-C$_3$H$_7$(i) | F | C | D |
| H | 2-CH$_3$-phenyl with C$_3$H$_7$(i) | F | C | D |
| 4-CH$_3$O— | 2,2-dimethylbenzodioxole-type | E | A | B |
| 4-Cl— | 2,2-dimethylbenzodioxole-type | E | A | B |
| 2-CH$_3$— | 2,2-dimethylbenzodioxole-type | E | A | B |

-continued

| Compound -COOR1) | | Activity against | | |
| --- | --- | --- | --- | --- |
| R | R1 | Laspeyresia pomonella L1-larvae | Myzus persicae | Aphis craccivora |
| H | (4-methylphenyl-CH(O-CH2-CH2-O) dioxolane) | F | C | D |
| H | (CH=CH-C(CH3)=N-N(C3H7(i))-) pyrazole | G | C | D |
| H | (pyrimidine with CH3, CH3, N(CH3)2) | G | C | D |
| H | (thiadiazole -C(=N-N-C2H5)-S-C2H5) | F | C | D |
| 2,3-CH2OCH2OCH2— | (phenyl with O-C(CH3)2-CH2 isopropylidenedioxy) | E | A | B |

A: 70–100% mortality with 1 ppm of active substance,
B: 70–100% mortality with 5 ppm of active substance.
C: 70–100% mortality with 10 ppm of active substance,
D: 70–100% mortality with 25 ppm of active substance,
E: 70–100% mortality with 50 ppm of active substance,
F: 70–100% mortality with 100 ppm of active substance,
G: 70–100% mortality with 200 ppm of active substance, and
H: 70–100% mortality with 400 ppm of active substance.

What is claimed is:

1. A compound of the formula

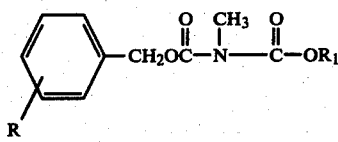

wherein
R is hydrogen, halo, alkyl of 1 to 4 carbon atoms, alkoxy of 1 to 4 carbon atoms, nitro or 2,3-methylenedioxy; and
R1 is a phenyl, dihydrobenzofuryl, or naphthyl group, said group being unsubstituted or substituted with alkyl of 1 to 4 carbon atoms, alkoxy of 1 to 4 carbon atoms, alkylthio of 1 to 4 carbon atoms, alkoxyalkyl of up to 4 carbon atoms in each of the alkoxy and alkyl portions, alkylthioalkyl of up to 4 carbon atoms in each alkyl portion, halo, amino, methylamino, dimethylamino, cyano, nitro, ethylenedioxymethyl, dimethylaminomethylideneamino, 1-methoxy-2-chloroethoxy or 1-methoxyprop-2-yl, or in addition in the case of phenyl, 2,3 or 3,4-methylenedioxy and 2,3 or 3,4-isopropylidenedioxy.

2. A compound according to claim 1 wherein when R1 is substituted phenyl, the substituents are alkyl of 1 to 4 carbon atoms alkoxy of 1 to 4 carbon atoms, ethylthiomethyl, ethoxymethyl, dimethylamino, 1-methoxyprop-2-yl, ethylenedioxymethyl, dimethylaminomethylideneamino or isopropylidenedioxy.

3. A compound according to claim 2 wherein R is hydrogen, halo, nitro, methyl, methoxy or 2,3-methylenedioxy.

4. A compound according to claim 1 wherein $R_1$ is 2,2-dimethyl-2,3-dihydrobenzofuranyl and R is hydrogen, methyl, methoxy, nitro or 2,3-methylenedioxy.

5. The compound according to claim 1 of the formula

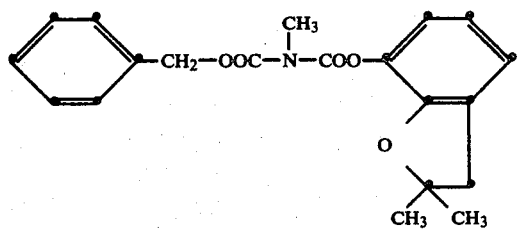

6. The compound according to claim 1 of the formula

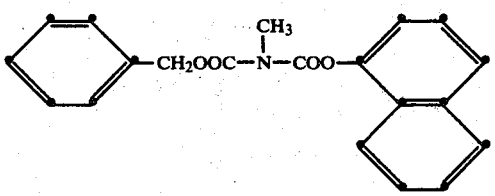

7. The compound according to claim 1 of the formula

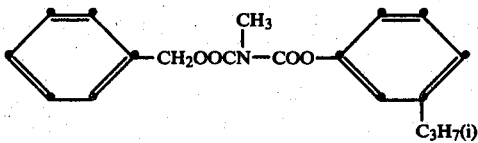

8. The compound according to claim 1 of the formula

9. An insecticidal and acaricidal composition comprising an insectidally or acaricidally effective amount of a compound according to claim 1 and a carrier therefor.

10. The method of combating insects and acarids which comprises applying an insectidally or acaricidally effective amount of a compound according to claim 1 to the locus of insects or acarids.

* * * * *